US00PP20756P2

(12) United States Plant Patent
van Noort

(10) Patent No.: US PP20,756 P2
(45) Date of Patent: Feb. 16, 2010

(54) ***ECHINACEA* PLANT NAMED 'IRRESISTIBLE'**

(50) Latin Name: *Echinacea purpurea*
Varietal Denomination: Irresistible

(76) Inventor: Marco van Noort, Wasbeeklaan 13, 2361 HG Warmond (NL)

( * ) Notice: Subject to any disclaimer, the term of this patent is extended or adjusted under 35 U.S.C. 154(b) by 0 days.

(21) Appl. No.: 12/313,801

(22) Filed: Nov. 25, 2008

(51) Int. Cl.
*A01H 5/00* (2006.01)

(52) U.S. Cl. ..... Plt./428
(58) Field of Classification Search ..... Plt./263, Plt./428
See application file for complete search history.

*Primary Examiner*—Susan B McCormick Ewoldt
(74) *Attorney, Agent, or Firm*—Penny J. Aguirre

(57) ABSTRACT

A new cultivar of hybrid *Echinacea*, 'Irresistible', characterized by its anemone-type inflorescences with orange colored ray florets and red-orange disk florets, its stems that are strong, upright and purple in color, and its resistance to viral diseases.

2 Drawing Sheets

Botanical classification: *Echinacea purpurea.*
Variety denomination: 'Irresistible'.

BACKGROUND OF THE INVENTION

The present Invention relates to a new and distinct cultivar of *Echinacea purpurea* and will be referred to hereafter by its cultivar name, 'Irresistible'. 'Irresistible' represents a new purple coneflower, an herbaceous perennial grown for landscape use.

The new cultivar arose from an ongoing breeding program conducted by the Inventor in a designated field at his nursery in Warmond, The Netherlands. In 2006, the Inventor pollinated the cultivar 'Razmatazz' (U.S. Plant Pat. No. 13,894) with pollen collected from numerous unnamed and unpatented selections of *Echinacea purpurea* with orange colored ray florets (single) and selections with semi-double inflorescences. The exact male parentage is unknown. 'Irresistible' was selected by the Inventor as a single unique plant amongst the resulting seedlings in June of 2008.

Asexual reproduction of the new cultivar was first accomplished by in vitro propagation in Rijswijk, The Netherlands in 2008 under the direction of the Inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Irresistible' from other cultivars of *Echinacea* known to the Inventor.

1. 'Irresistible' exhibits an anemone-type inflorescence form (double) with orange colored ray florets and disk florets that are red-orange in color, each with an enlarged petal.
2. 'irresistible' exhibits strong, upright stems that are purple in color.
3. 'Irresistible' has been shown to be resistant to viruses.

The new cultivar is similar to its female parent plant, 'Razzmatazz' in having anemone type inflorescences, however 'Razzmatazz' differs in inflorescence color in having ray florets that are dark pink and disk florets that are red-purple. 'Irresistible' also differs from 'Razzmatazz' in having sturdier stems and a greater resistance to viruses. The possible male parents are either single or semi-double and lack the full anemone inflorescence form as exhibited with 'Irresistible'. The closest comparison cultivar is 'Hot Papaya' (U.S. Plant patent application Ser. No. 12/319,413), which also exhibits orange colored inflorescences. 'Hot Papaya' differs, at a minimum, in having red-orange disk florets that turn orange in the center region of the Capitulum.

BRIEF DESCRIPTION OF THE DRAWING

The plants and plant parts in the accompanying photographs depict a one year-old plant of 'Irresistible' as grown outdoors in a test garden in Warmond, The Netherlands.

The photograph in FIG. 1 provides a side view of 'Irresistible' in bloom.

Figure 2:
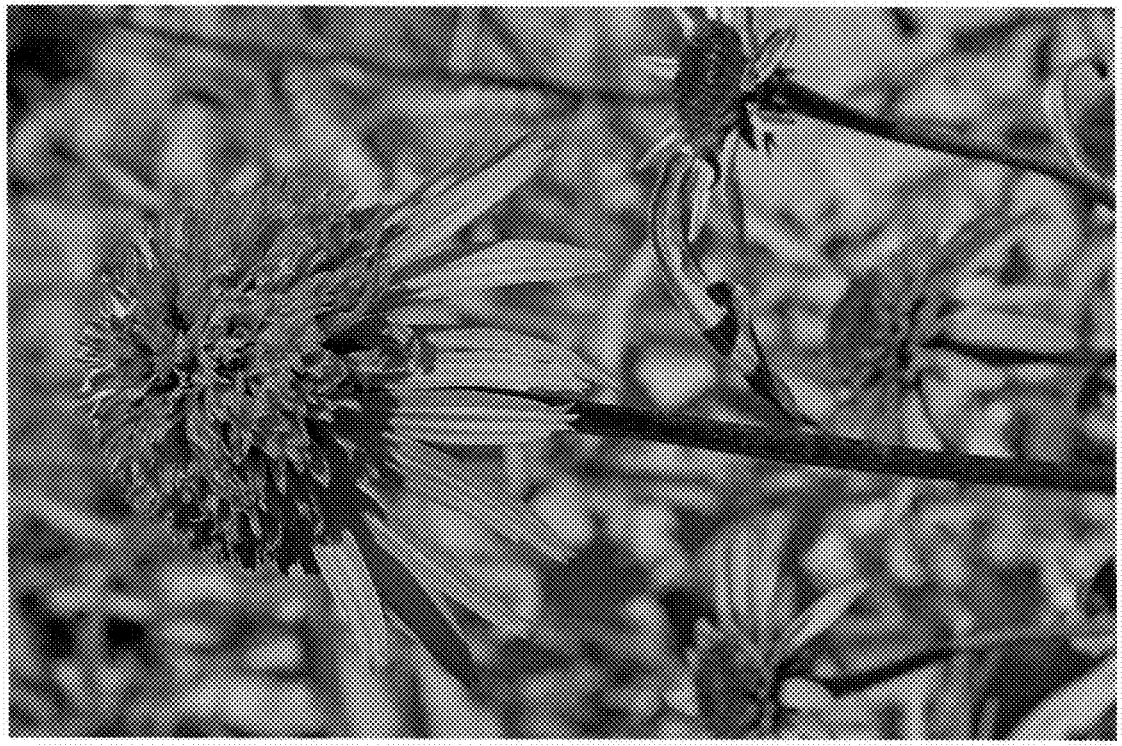

The photograph in FIG. 2 shows a close-up of an inflorescence of 'Irresistible'.

Figure 1:
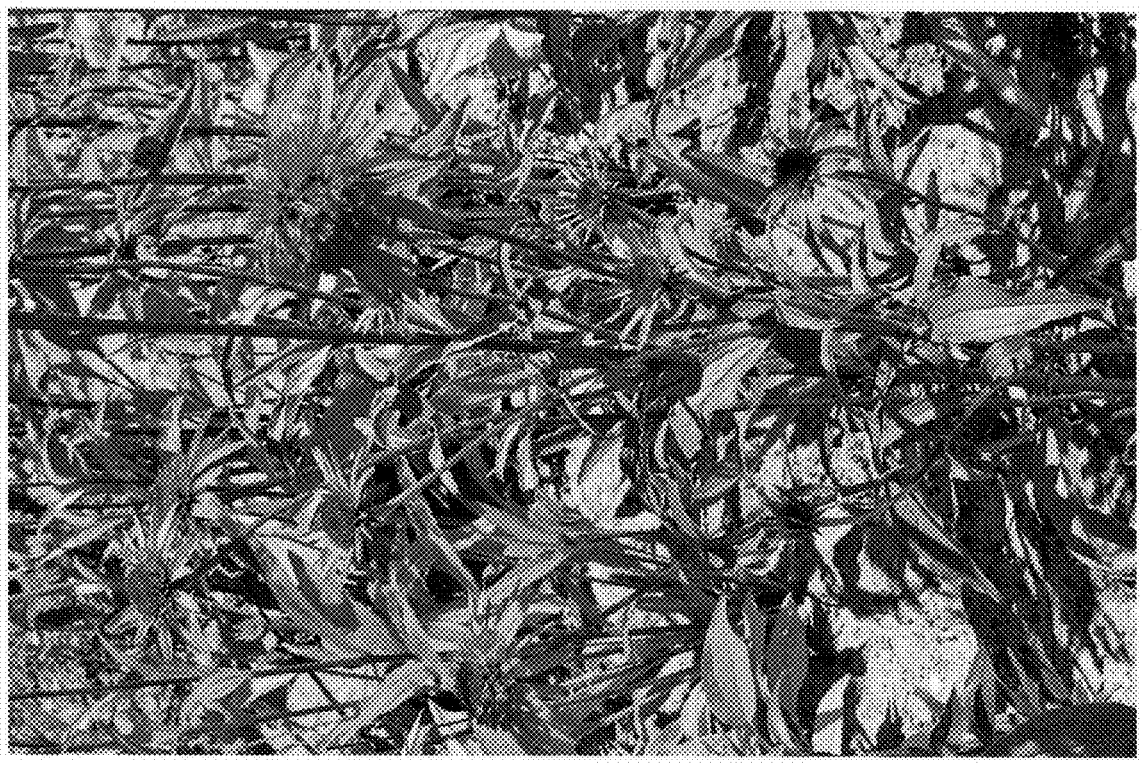
Figure 3:
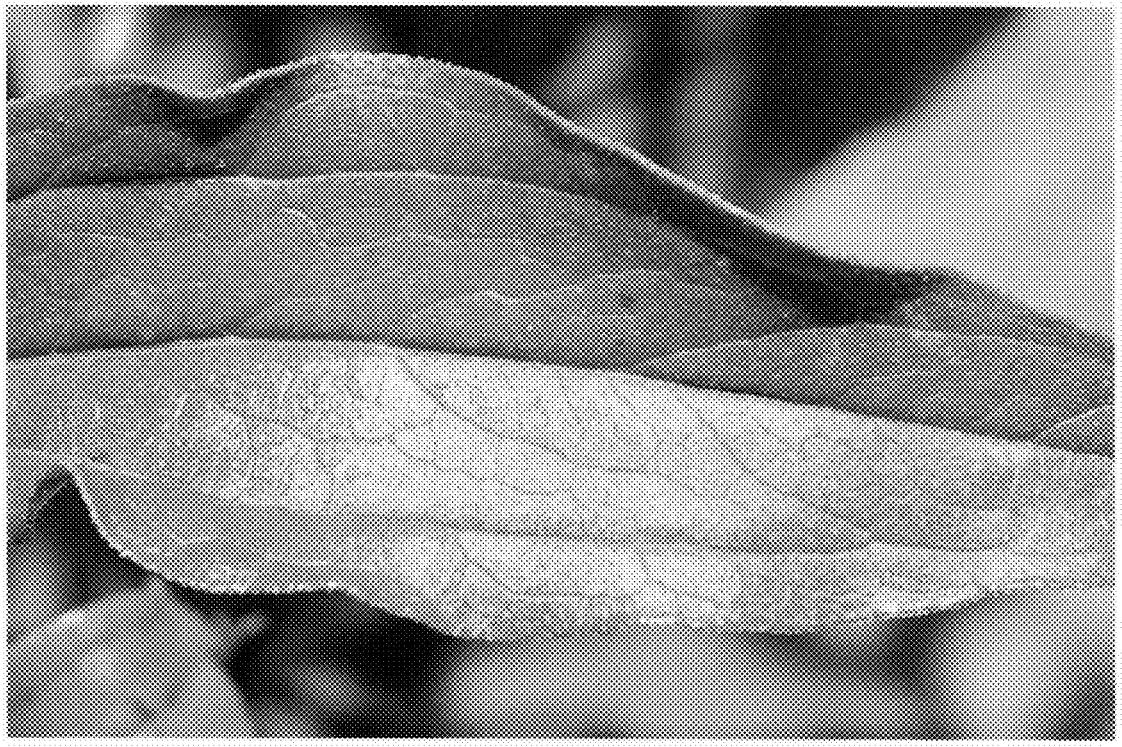

The photograph in FIG. 3 provides a close-up view of a leaf of 'Irresistible'.

The Colors in the photograph may differ slightly from the color values cited in the detailed botanical description, which accurately describe the colors of the new *Echinacea.*

BOTANICAL DESCRIPTION OF THE PLANT

The following is a detailed description of a one-year-old plant of the new cultivar as grown outdoors in a test garden in Warmond, The Netherlands. The plants were grown under average day temperatures of 12° to 30° C. and average night temperatures of 4° to 16° C. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Blooming period.*—Continuously from early June to early September.

*Plant habit.*—Herbaceous perennial, clump forming, upright.

*Height and spread.*—Reaches about 75 cm in height and 30 cm in spread when grown with good fertility.

*Hardiness.*—U.S.D.A. Zones 3 to 9.

*Diseases resistance.*—Has shown resistance to viruses.

*Root description.*—Fibrous.

Growth and propagation:

*Propagation.*—Division, vegetative stem cuttings, and tissue culture.

*Growth rate.*—Moderately vigorous.

Stem description:

*Shape.*—Sightly oval, solid.

*Stem color.*—145B, strongly tinged with 177A to 177B.

*Stem size.*—Lateral stems are an average of 6 mm in diameter and an average of 45 cm in height excluding peduncles.

*Stem strength.*—Strong.

*Stem aspect.*—Held upright.

*Stem surface.*—Moderately rough to touch and sparsely covered with short strigose hairs about 0.8 mm in length and 155C in color.

*Stem number.*—Average of 3.

*Internode length.*—Average of 6.8 cm in length.

*Branching.*—Main flowering stem with an average of 3 lateral branches.

Foliage description:

*Leaf shape.*—Lanceolate to narrowly ovate.

*Leaf division.*—Simple.

*Leaf base.*—Attenuate to narrowly cuneate.

*Leaf apex.*—Narrowly acute.

*Leaf venation.*—Tri-nerved, 147D on upper and lower surface.

*Leaf margins.*—Entire and sinuate.

*Leaf attachment.*—Petiolate on lower leaves and sessile on upper leaves.

*Leaf arrangement.*—Alternate.

*Leaf size.*—Average of 10.8 cm in length and 2.7 cm in width.

*Leaf color.*—Newly formed upper surface; 143A, newly formed lower surface; a color between 144A and 146A, mature upper surface; 146A, mature lower surface; 146B.

*Leaf surface.*—Upper surface is moderately glossy, lower surface is slightly glossy, both surfaces are moderately covered with short strigose hairs about 0.3 mm in length and 157D in color.

*Petioles.*—V-shaped, an average of 2.6 cm in length and 3 mm in width, 145B in color on both surfaces, surface is pubescent.

Flower description:

*Type.*—Capitulum, heterogamous with ray florets around the head margin and disk florets with expanded petal in the center, anemone-type (also referred to as double).

*Capitulum number.*—Average of 3 per stem.

*Lastingness of inflorescence.*—About 2 to 3 weeks.

*Capitulum size.*—Matures to about 6.1 cm in depth and 9.6 cm in diameter, disk is about 5.7 cm in diameter.

*Fragrance.*—Faint, acid-sweet.

*Involucral bracts or phyllary.*—About 50 arranged in 3 overlapping rows, average of 1 cm in length and 3 mm in width, cuneate base, acute apex, narrowly ovate in shape, upper surface is 146A in color and 144A near base, lower surface is 143A to 143B in color, margins entire and sparsely covered with short hairs about 0.2 mm in length and 157D in color, surface is dull on both surfaces.

*Buds.*—Flatten globular in shape, up to 1.9 cm in diameter and 1.5 cm in height, color between 143A and 146A with immature ray florets 150B to 151C.

*Peduncle.*—Strong, terminal is an average of 11.4 cm in length and 4 mm in diameter with axillary peduncles an average of 4.7 cm in length and 4 mm in diameter, 145B in color and tinged with 177B, surface is sparsely covered with short strigose hairs about 0.8 mm in length and 155C in color.

*Ray florets* (*sterile*).—Average of 20 in single row, narrow oblanceolate in shape, vertical ridges on both surfaces, about 4.9 cm in length and 8 mm in width, emarginate to praemorse apex, cuneate base, entire margin except apex, smooth and dull surface on both surfaces, reflexed as they mature to about 30° from horizontal, color of upper surface when opening; 26A with base 26B, color of lower surface when opening; N34B with base N34C, color of upper surface when fully open; 34B with base N34C, color of lower surface when mature; 53D to 58A, non fading.

*Disk flowers* (*bisexual*).—Numerous, about 400, tubular in shape with one petal expanded like a ray floret, arranged spirally on a deltoid-shaped receptacle, about 1.8 mm in height and 1.1 cm in width and 155B in color, apex is strongly praemorse, fused base, entire margin, average of 2.2 cm in length and 7 mm in width, surface of upper surface is smooth and dull, surface of lower surface is smooth and slightly glossy, color when opening upper surface; 31B with apex 31A and margins N34A, color of lower surface when opening; 32D with margins n34A, color of upper surface when fully open; 34A with base 34C, color of lower surface when fully open; N34C with apex N34A to N34C.

*Disk spines.*—Average of 400, acicular in shape, acute apex, attenuate base, smooth and glossy surface, color is 45A at apex, 28B in mid region and 144C at base.

Reproductive organs (present on disk florets only):

*Gynoecium.*—Pistil; 1, 6.5 mm in length, style; about 5 mm in length and 41D) in color, stigma; unequal, decurrent and 41D in color, ovary; 157A to 157B in color.

*Androcoecium.*—Stamens; 2, filaments; 3 mm in length and 164C to 164D in color, anthers; about 1.8 mm in length and N199B in color, pollen; low in quantity not distinguishable in color.

*Fruit/seed.*—No seed production has been observed.

It is claimed:

1. A new and distinct cultivar of *Echinacea* plant named 'Irresistible' substantially as herein illustrated and described.

* * * * *